United States Patent
Bae et al.

(10) Patent No.: US 7,221,137 B2
(45) Date of Patent: May 22, 2007

(54) APPARATUS WITH STORAGE FOR MEASURING STRAY CURRENTS FROM SUBWAY RAILS AND POWER LINES

(75) Inventors: Jeong Hyo Bae, Gimhae-si (KR); Dae Kyeong Kim, Gimhae-si (KR); Tae Hyun Ha, Changwon-si (KR); Hyun Goo Lee, Changwon-si (KR); Yun Cheol Ha, Gimhae-si (KR)

(73) Assignee: Korea Electrotechnology Research Institute, Kyungsangnam-Do (KR)

( * ) Notice: Subject to any disclaimer, the term of this patent is extended or adjusted under 35 U.S.C. 154(b) by 0 days.

(21) Appl. No.: 10/989,553

(22) Filed: Nov. 17, 2004

(65) Prior Publication Data

US 2005/0127891 A1    Jun. 16, 2005

(51) Int. Cl.
G01R 31/02    (2006.01)

(52) U.S. Cl. .................. 324/72; 324/71.2; 324/72.5; 324/425

(58) Field of Classification Search .................. 324/72, 324/71.2
See application file for complete search history.

(56) References Cited

U.S. PATENT DOCUMENTS

| | | | | |
|---|---|---|---|---|
| 4,437,065 A | * | 3/1984 | Woudstra | ............... 324/425 |
| 5,418,812 A | * | 5/1995 | Reyes et al. | ............... 375/130 |
| 6,160,403 A | * | 12/2000 | Kajiyama | ............... 324/425 |
| 6,236,952 B1 | * | 5/2001 | Jun et al. | ............... 702/119 |
| 6,822,432 B2 | * | 11/2004 | Hilleary | ............... 324/72 |
| 6,833,709 B2 | * | 12/2004 | Xie | ............... 324/434 |

* cited by examiner

*Primary Examiner*—Andrew H. Hirshfeld
*Assistant Examiner*—John Zhu
(74) *Attorney, Agent, or Firm*—Rothwell, Figg, Ernst & Manbeck

(57) ABSTRACT

A measuring apparatus with storage that measures and analyzes both stray currents from subway rails or power lines and the pipe-to-soil voltage of a buried metallic structure simultaneously is disclosed. The data measuring apparatus with storage for measuring stray currents from subway rails or power lines and the pipe-to-soil voltage of a buried metallic structure in accordance with the present invention comprises measuring means, which is a portable module that allows easy installation at one or multiple measurement points of the buried metallic structure, for measuring stray currents from the subway rails or power lines and the pipe-to-soil voltage of a buried metallic structure simultaneously and for storing and transmitting the measurement data and analytic computing means for receiving the measurement data transmitted from the measuring means and for databasing and graphically displaying the received measurement data for time-synchronous data analysis.

12 Claims, 6 Drawing Sheets

APPARATUS WITH STORAGE FOR MEASURING STRAY CURRENTS FROM SUBWAY RAILS AND POWER LINES

FOREIGN PRIORITY

The present invention claims priority under 35 U.S.C. 119 on Korean Application No. 10-2003-078604 filed Nov. 17, 2003; the contents of which are incorporated by reference in their entirety.

BACKGROUND OF THE INVENTION

1. Field of the Invention

The present invention relates to a stand-alone measuring apparatus capable of measuring stray currents from subway rails and power lines and the pipe-to-soil voltage of a buried metallic structure, and more particularly, but not by way of limitation, to a measuring apparatus with storage that allows simultaneous analysis of the relation between stray current from subway rails and the resulting pipe-to-soil voltage of a buried metallic structure and the relation between stray current from power lines and the resulting pipe-to-soil voltage of a buried metallic structure.

2. Description of the Related Art

Corrosion is the chemical or electrochemical reaction between a material, usually a metal, and its environment that produces a deterioration of the metal and its properties. Corrosion of a metal is often called electrochemical corrosion because it is caused by an electrochemical reaction involving a flow of electrons between cathodic and anodic areas.

The electrochemical corrosion arises from naturally occurring processes at specific locations on a metallic structure involving electrical current flow into the ambient soil electrolyte from anodes where oxidation reactions occur. The current flows to sites on the structure acting as cathodes where reduction reactions occur. Four components of the electrochemical corrosion are an anode, a cathode, an electrical path or metallic path, and an ionic path or electrolyte.

Methods for detecting corrosion of a metal include the sonic reflection method, the ultrasonic test method, the LPR (linear polarization resistance)method, the ER (electrical resistance) method, and the electrochemical potential measurement method. The sonic reflection method locates cracks or corrosion of a metal by collecting a sonic beam reflected by the metal using an array sensor and analyzing the collected data. The ultrasonic test method inspects corrosion of a metal by detecting changes in the thickness of the metal reduced by the corrosion. The LPR method detects the instantaneous corrosion rate of a metal by inserting a test probe into a conductive fluid and measuring the polarization resistance. The ER method measures the corrosion rate of a metal by inspecting changes in the electrical resistance of the metal caused by long-term electrochemical corrosion. The electrochemical potential measurement method detects the corrosion of a metal by measuring the electrochemical potential of the metal. The electrochemical potential measurement method is the most widely used method.

The electrochemical potential measurement method involves the measurement of the electrochemical potential difference between a buried metallic structure, which is a working electrode, and a reference electrode (Cu/CuSO4, CSE) in an electrical contact with ground above the structure, which is an electrolyte. The potential is measured with the positive and negative terminals of a measuring instrument connected to the reference electrode and the metallic structure respectively and then the sign of the measured value is reversed. The potential value is used to determine the level of the electrochemical corrosion. For example, a potential (e.g., −1000 mV) less than the cathodic protection criteria (−850 [mV/CSE], 250 [mV/Zn] in case of a zinc reference electrode) indicates that the metallic structure is protected from the corrosion. A potential greater than the cathodic protection criteria indicates that the metallic structure is corroding away.

Conventionally, to check the status of buried or submerged structures such as gas pipelines, tanks, and water pipelines, corrosion inspection of such structures has been conducted on a regular/irregular basis.

The corrosion inspection is conducted intermittently by a human inspector using a portable tester or a portable strip chart recorder. A shortcoming of such a corrosion inspection is that it takes lots of time because the human inspector need to connect test leads to a test box, the location of which is normally on the street, for the corrosion potential measurement (−terminal to the pipe and +terminal to the reference electrode) and to move to a position which allows easy and safe measurement.

For the reason, a corrosion inspection instrument that can be inserted into the test box for the corrosion potential measurement, which was developed by the inventor of the present invention, has been used recently.

Corrosion protection generally means the elimination of one or more sources that cause the corrosion. Because it is practically impossible to eliminate all the sources of the corrosion completely, methods that can mitigate the electrochemical corrosion reaction using inhibitors, insulators, etc are commonly employed. Cathodic protection is one of the most popular corrosion protection methods.

Cathodic protection provides corrosion protection to any bare metal areas exposed to soil by causing direct current (DC) to flow from the soil into the metallic structure, thereby polarizing the metallic structure as a cathode.

It is possible to cathodically protect a metallic structure by an external power supply such as a rectifier that generates an impressed current through the soil from an anode to the protected object. The rectifier provides direct current (DC) to the protected structure in order to maintain the electrochemical potential of the protected structure below the cathodic protection criteria (e.g., −850 mV/CSE). In other words, if the potential difference between a buried metallic structure and the reference electrode measured by a portable tester or a portable strip chart recorder is greater than the cathodic protection criteria, the rectifier provides direct current (DC) to the protected structure through an insoluble anode (high silicon cast iron (HSCI)) and the soil, so that the potential difference may remain below the cathodic protection criteria to protect the metallic structure from the electrochemical corrosion.

If interference by stray currents from subway rails or power lines occurs, the pipe-to-soil voltage will fluctuate as shown in FIG. 6 or the third harmonic will be found as shown in FIG. 7, respectively. The subway power system is designed such that the current is provided to subway trains from a subway power substation through power feeder cables and the current returns to the subway power substation through rails after driving the subway trains.

In the subway power system, a portion of the current deviates from the designed path and leaks into the soil because of the longitudinal resistance of the rails and incomplete insulation between the rails and the soil. The current flowing into the soil is called stray current.

The stray current flows along the length of a metallic structure buried in the soil (e.g., gas pipeline, oil pipeline, water pipeline) acting as a conductor and leaks into the soil at some specific locations which are near the cathode or have low soil resistivity. The leakage current returns to the negative feeder of the subway power supplying system. Corrosion occurs intensively around such locations.

The corrosion caused by stray currents from the subway is called stray current corrosion or electrolytic corrosion. With a view to preventing the stray current corrosion, the magnitude of the interference and the positions in which the interference occurs are analyzed by measuring only the pipe-to-soil voltage of a buried metallic structure.

Stray currents from power lines are affective by various types of induction such as capacitive induction, inductive induction, and resistive induction. AC induction voltage caused by resistive induction is dominant at places where the aforementioned apparatuses for measuring the pipe-to-soil voltage are employed.

There is a resistive coupling effect between a grounding structures (rods, wires, mesh) and a buried metallic structure sharing the same electrolyte (soil), whereby energy can be transmitted between the two structures in the form of AC voltage or current. In an electrical power system having a grounded neutral wire, unbalanced current due to power system unbalanced or third harmonic currents may flow along the neutral wire. In this case, the energy is transmitted from the ground point to the buried metallic structure through the soil. If the buried metallic structure is coated with an insulator, a resistive induction voltage is generated between the metallic structure and the ground point.

Suppose that a grounding conductor of the power system is a hemisphere of radius r as shown in FIG. 9. A voltage induced at a distance of x from O (the center of the hemisphere) when current I flows into the soil having a constant resistivity can be computed as follows.

Ohm's law states that the induced voltage v is expressed by $$v = IR \quad (1)$$

and since $R = \int dR = \int \rho(dr/2\pi r2)$, the induced voltage v is equivalently given by $$v = \rho I / 2\pi x \quad (2)$$

The induced voltage v expressed by the equation (2) is induced at a pipe located at a distance of x from the grounding conductor providing current I to the soil.

As the equation (2) indicates, the magnitude of the induced voltage depends on the resistivity of the soil and the distance between the grounding conductor and the pipe if the current flowing into the soil through the ground remains constant.

In Korean power distribution systems, in which the primary voltage is 22,900 V, a 3-phase 4-wire system with multiple grounding of the neural wire is employed as shown in FIG. 10. Therefore, the problematic AC stray current is caused by the multiple grounding wires at a neutral point.

In the 3-phase 4-wire system, the fourth wire, i.e., the neutral wire is repeatedly grounded at regular intervals and is designed such that 60 Hz current does not flow through the neutral wire. However, in the case where a third harmonic component is generated due to an unbalanced load condition, some of the third harmonic current flows through the neutral wire and some of the harmonic current flows through the ground.

Because a buried pipeline is a good grounding conductor, the third harmonic current tends to flow into the pipe by the resistive coupling effect. The current inflow depolarizes the polarization on the surface of the pipe and increases the consumption rate of Mg anodes. Moreover, it may give an electric shock to pipeline workers and cause an explosion accident by an electric arc in case of an accidental arc.

For these reasons, the pipe-to-soil voltage of a buried metallic structure is measured on a regular basis using a portable measuring instrument or a corrosion inspection system developed by the inventor of the present invention to inspect whether the metallic structure is protected from corrosion.

Unfortunately, however, the apparatuses used for corrosion inspection were not capable of directly measuring the stray current and thus it was impossible to analyze the stray current.

It is possible to measure the stray current using an oscilloscope. To use an oscilloscope for the stray current measurement, however, the oscilloscope needs to be installed at a subway station while the subway is out of service and the measurement data needs to be collected after the measurement is completed.

However, oscilloscopes are expensive and not easy to install around subway rails because oscilloscopes are relatively big in size. To measure the stray current, it is required to install a plurality of oscilloscopes in multiple measurement points, which is almost impossible for practical reasons.

In conventional corrosion inspection methods which simply measure the pipe-to-soil voltage of a buried metallic structure, the positions where current leakage occurs and the magnitude of the stray current cannot be precisely detected.

Consequently, a small-sized and low-cost stand-alone measurement apparatus that can easily measure the stray currents from subway rails at a rail impedance bond and analyze the stray current is quite in need.

SUMMARY OF THE INVENTION

In view of the shortcomings of the prior art, it is an object of the present invention to provide a measuring apparatus with storage that measures and analyzes both stray currents from subway rails or power lines and the pipe-to-soil voltage of a buried metallic structure simultaneously.

It is another object of the present invention to provide a measuring apparatus with storage that measures stray currents from subway rails and power lines at multiple locations simultaneously and stores the measured information for analysis.

The data measuring apparatus with storage for measuring stray currents from subway rails or power lines and the pipe-to-soil voltage of a buried metallic structure in accordance with the present invention comprises measuring means, which is a portable module that allows easy installation at a measurement point of the buried metallic structure, for measuring stray currents from the subway rails or power lines and the pipe-to-soil voltage of a buried metallic structure simultaneously and for storing and transmitting the measurement data and analytic computing means for receiving the measurement data transmitted from the measuring means and for databasing and graphically displaying the received measurement data for data analysis.

BRIEF DESCRIPTION OF THE DRAWINGS

The above features and other advantages of the present invention will be more clearly understood from the following detailed description taken in conjunction with the accompanying drawings, in which.

DETAILED DESCRIPTION OF THE PREFERRED EMBODIMENTS

In order that the invention may be fully understood, preferred embodiments thereof will now be described with reference to the accompanying drawings.

Figure 1:
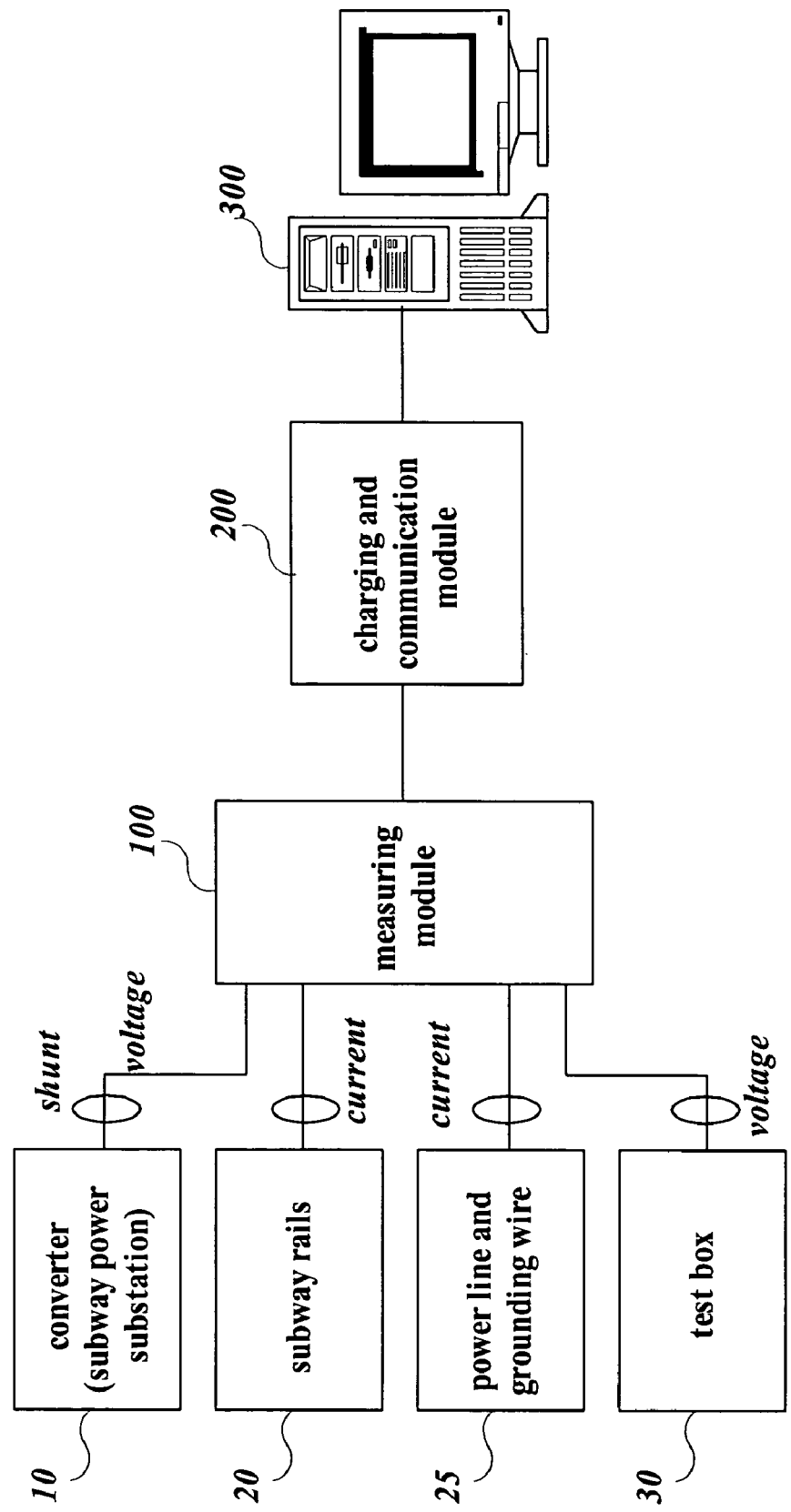
FIG. 1 illustrates a block diagram of a data measuring apparatus with storage for measuring stray currents from subway rails and power lines in accordance with the present invention.

FIG. 1 illustrates a block diagram of a data measuring apparatus with storage for measuring stray currents from subway rails and power lines in accordance with the present invention. The apparatus comprises a measuring module 100, a charging and communication module 200, and an analyzing computer terminal 300.

Figure 4A:
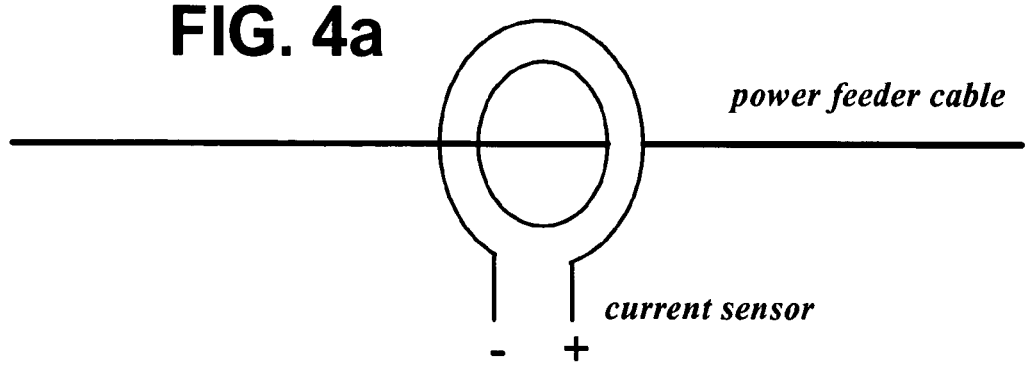
FIG. 4a illustrates an example of measuring stray current from subway power lines using a current sensor.

The measuring module 100 measures stray currents using a clamp-on type current sensor (114 in FIG. 2), which can be attached to a power feeder cable connected to rails 20 extended from a converter 10 installed in a subway power substation. The measuring module 100 measures the stray currents by detecting current changes in the power feeder cable using the current sensor attached to specific positions of the power feeder cable, as shown in FIG. 4a. The measurement is conducted at an impedance bond of the rails and a converter negative feeder.

Figure 4B:
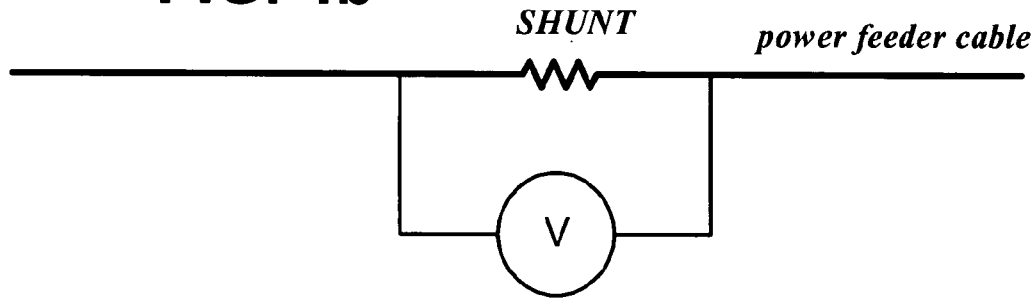
FIG. 4b illustrates an example of generating a voltage signal for measuring stray current from a subway power substation.

The measuring module 100 also measures stray currents using voltage across a shunt resistor connected to the power feeder cable from the converter 10. As shown in FIG. 4b, a shunt resistor is connected in series with the power cable from the converter 10 and the voltage across the shunt resistor is measured using a voltmeter V connected in parallel with the shunt resistor.

The measuring module 100 analyzes the pipe-to-soil voltage by receiving a voltage signal obtained by the same configuration shown in FIG. 4b, but without the shunt, from a test box 30 for measuring the corrosion voltage.

The measuring module 100 also measures the stray currents from a ground line 25 and a power line other than the power line providing power to the subway using the clamp-on type current sensor as shown in FIG. 4a. The measurement is conducted at a grounding wire of a neutral wire of a power distribution line.

The charging and communication module 200 charges batteries for powering the measuring module 100 and communicates with the analyzing computer terminal 300 using a communication port.

Driven by AC 220V/60 Hz power, the charging and communication module 200 can charge up to 4 measuring modules 100 simultaneously using 4 charging ports. The charging and communication module 200, which is equipped with 4 USB communication ports, can communicate with 4 measuring modules 100 and the computer terminal 300. Each charging port possesses a lamp indicating that the port is being charged or completely charged.

The charging and communication module 200 provides charging power and communicates with the measuring module 100 both by wire. However, the charging and communication module 200 and can perform wireless communication with a plurality of the measuring modules 100 using a wireless communication apparatus such as Bluetooth or a wireless network interface such as Access Point.

Communicating with the measuring module 100 through the charging and communication module 200, the analyzing computer terminal 300 collects the measured stray current and pipe-to-soil voltage, stores the measured data in a database, and displays the measured data graphically.

Figure 2:
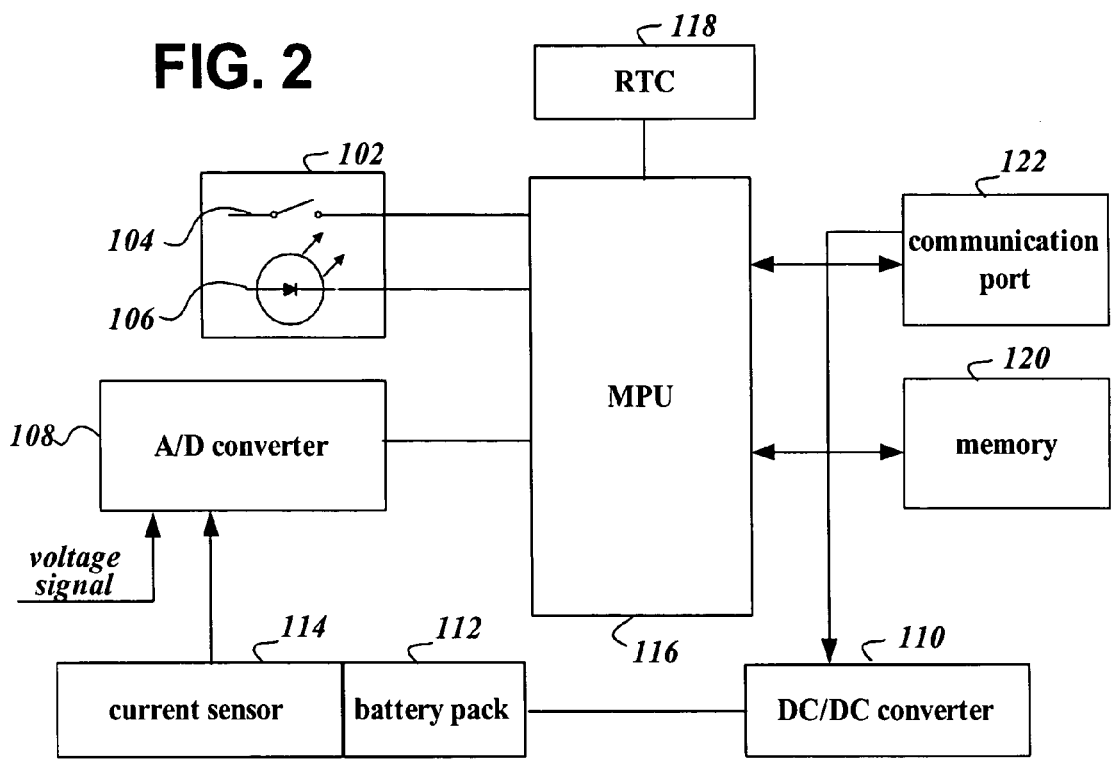
FIG. 2 illustrates a detailed block diagram of the measuring module in FIG. 1.

FIG. 2 illustrates a detailed block diagram of the measuring module 100, which comprises a function input unit 102, an A/D converter 108, a DC/DC converter 110, a battery pack 112, a main processor unit (MPU) 116, a serial real time clock (RTC) 118, a memory 120, and a communication port 122.

The function input unit 102 comprises a switch 104 for starting the measurement of stray currents and pipe-to-soil voltage and a display lamp 106 that is an LED for indicating the status of the switch 104.

The A/D converter 108 converts an analog voltage input from the test box 20, which is the measured pipe-to-soil voltage, into digital data of a predetermined resolution and converts an analog current input from the current sensor 114 into digital data of a predetermined resolution.

The DC/DC converter 110 converts a DC voltage input (e.g., 3V) from the charging and communication module 200 into a different DC voltage output (e.g., ±12V). The battery pack 112, which is charged by the DC voltage output of the DC/DC converter 110, provides DC power required for the measuring module 100 and the current sensor 114.

Powered by the battery pack 112, the current sensor 114 detects stray currents from subway rails 20 and the power feeder cable connected to converter 10.

The main processor unit (MCU) 116, which is an 8-bit microcontroller having a 4K×14 word program memory and a 256×8 byte data RAM, stores the stray currents and pipe-to-soil voltage data digitized by the A/D converter 108 in a memory 120 and provides the digitized data to the analyzing computer terminal 300 through the communication port 122. The serial real time clock (RTC) generates a system clock required for the operation of the main processor unit (MCU) 116.

The memory 120 is a flash memory of a size greater than 64 Mbytes in order to store the measurement data for at least 48 hours under the condition that 100 measurements are conducted for a second.

The communication port 122 is a USB port that can communicate with the analyzing computer terminal 300 through the charging and communication module 200 and transmits the stray currents and pipe-to-soil voltage measured by the measuring module 100 to the analyzing computer terminal 300.

Figure 3:
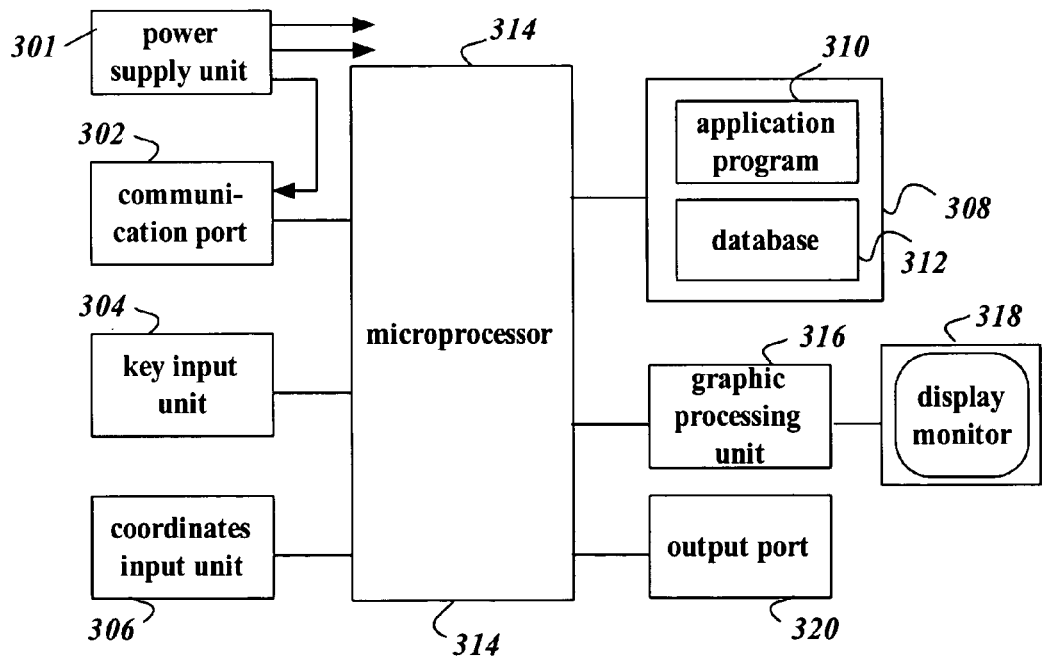
FIG. 3 illustrates a detailed block diagram of the analyzing computer terminal in FIG. 1.

FIG. 3 illustrates a detailed block diagram of the analyzing computer terminal 300, which comprises a power supply unit 301, a communication port 302, a key input unit 304, a coordinates input unit 306, a hard disk drive 308, a microprocessor 314, a graphic processing unit 316, a display monitor 318, and an output port 320.

The power supply unit 301 provides power required for the operation of the analyzing computer terminal 300 and is connected to the charging and communication module 200 through the communication port 302 in order to power the charging and communication module 200.

The communication port 302 is a USB port that is capable of powering and communicating with the charging and communication module 200 and receives the measured stray currents and pipe-to-soil voltage data from the measuring module 100 through the charging and communication module 200.

The communication port 302 includes a wireless communication port if it communicates with the charging and communication module 200 in a wireless way.

The key input unit 304 receives key input for analyzing the stray currents from subway rails and power lines and the measured pipe-to-soil voltage. The coordinates input unit 306, which is commonly the so-called mouse, receives coordinates input for analyzing the stray currents and the pipe-to-soil voltage.

The hard disk drive 308 contains an operation system such as Microsoft Windows and an application program 310 for measurement and analysis of the stray currents from subway rails and power lines and the pipe-to-soil voltage of a buried metallic structure. Also, the hard disk drive 308 contains the database 312 for storing the stray currents and pipe-to-soil voltage data provided periodically from the measuring module 100 in such a way that search operations can be performed.

The microprocessor 314, which executes the operating system, executes the application program 310 stored in the hard disk drive 308 and performs data processing to graphically display the measured data of stray currents and pipe-to-soil voltage.

Driven by the application program 310 executed by the microprocessor 314, the graphic processing unit 316 performs graphic processing to display the measurement data on the display monitor 318 in various graphical ways.

The output port 320, which is connected to an external device such as a printer, a data storage device, and a large-scale display apparatus, outputs the databased measurement data so that the measurement data may be printed by an external printer, stored in an external storage device, or displayed on an external large-scale display apparatus.

If multiple measuring modules are installed in more than one subway stations, a unique ID is assigned to each of the measuring modules. In this case, the analyzing computer terminal 300 executing the application program 310 can search for the measuring modules based on their IDs and set the station at which each measuring module is installed, measurement start time, measurement end time, and data sampling time for each measuring module in the application program. The measurement start time and end time should be precisely displayed in consideration of leap years.

The analyzing computer terminal 300 may erase the measurement data in the database 312 stored in the hard disk drive 308 and display the progress of data download from the measuring module 100 and data conversion with varying percentage values. The database 312 stored in the hard disk drive 308 allows a search for specific data by the measurement data, the measuring module ID, the station number, etc.

Executing the application program 310, the analyzing computer terminal 300, responsive to user input from the key input unit 304 or the coordinates input unit 306, graphically displays the measurement data stored in the database 312 with zoom-in/zoom-out functions. When the displayed data is zoomed in, the screen can be scrolled up and down so that the complete data may be displayed on the screen. Also, a reset zoom operation can be automatically executed to restore the original display status after a zoom-in operation is conducted.

Executing the application program 310, the analyzing computer terminal 300 may display the values of specific measurement data while a cursor moves on the graph according to user input from the coordinates input unit 306. When the measurement data is displayed, a grid may be displayed on the screen for the convenience of users. Each time measuring modules are switched from one to another for data display, information on the new measuring module such as the ID, station number, measurement start time, etc may be displayed. In addition, a plurality of measurement data may be simultaneously displayed in one graph.

The analyzing computer terminal 300 may convert current data into voltage data and vice versa when displaying the measurement data graphically. The x-axis of the graph corresponds to time. It is desirable that the resolution of the x-axis be 1/N second and thus the minimum time unit may be set from 1 second to $1/128$ second.

Stray currents from subway rails and power lines are detected by the current sensor 114 and the output of the current sensor 114 is digitized by the A/D converter 108 and stored in the memory 120.

Figure 5:
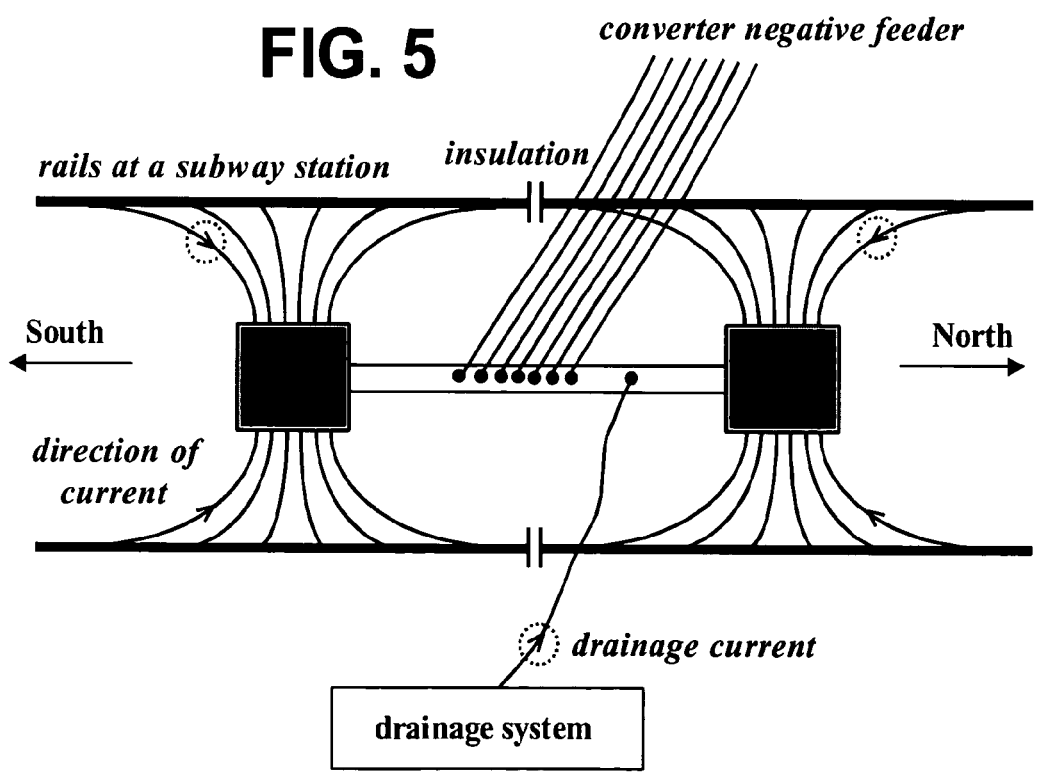
FIG. 5 illustrates an example of measuring stray current from subway rails using a current sensor.
Figure 6:
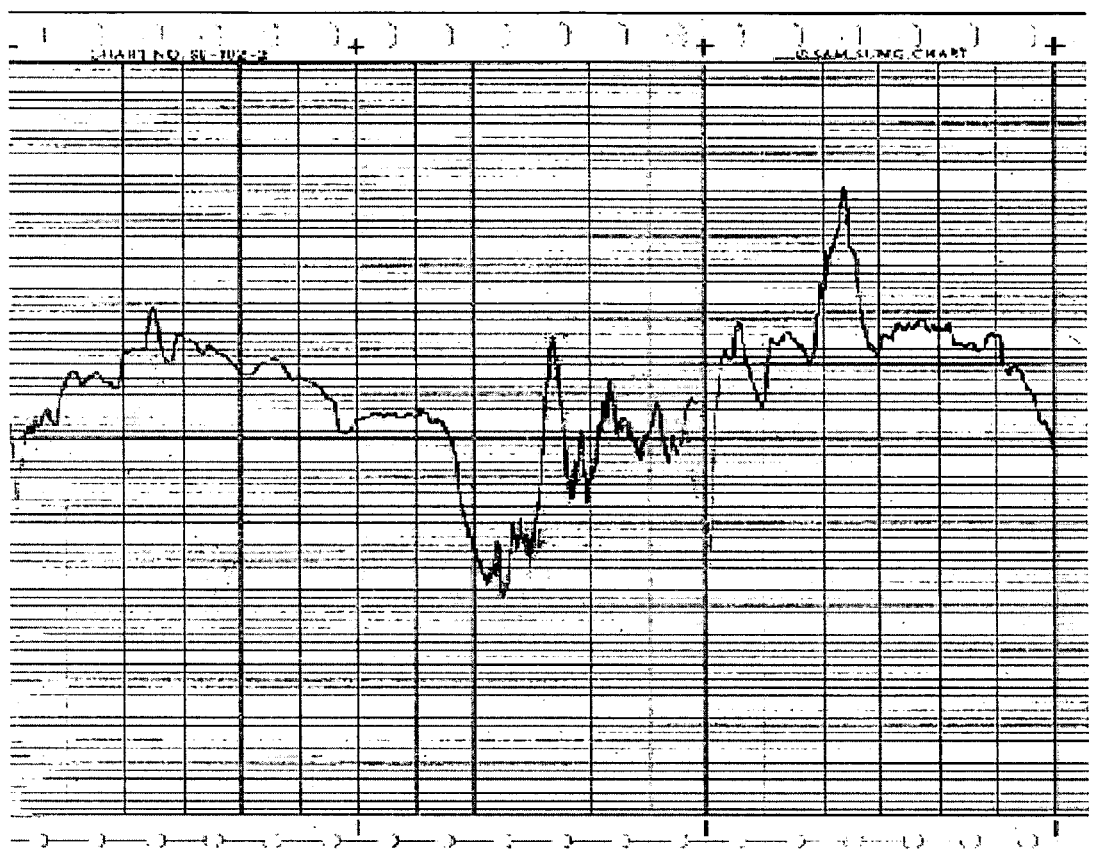
FIG. 6 illustrates pipe-to-soil voltage fluctuating by interference caused by stray currents.
Figure 7:
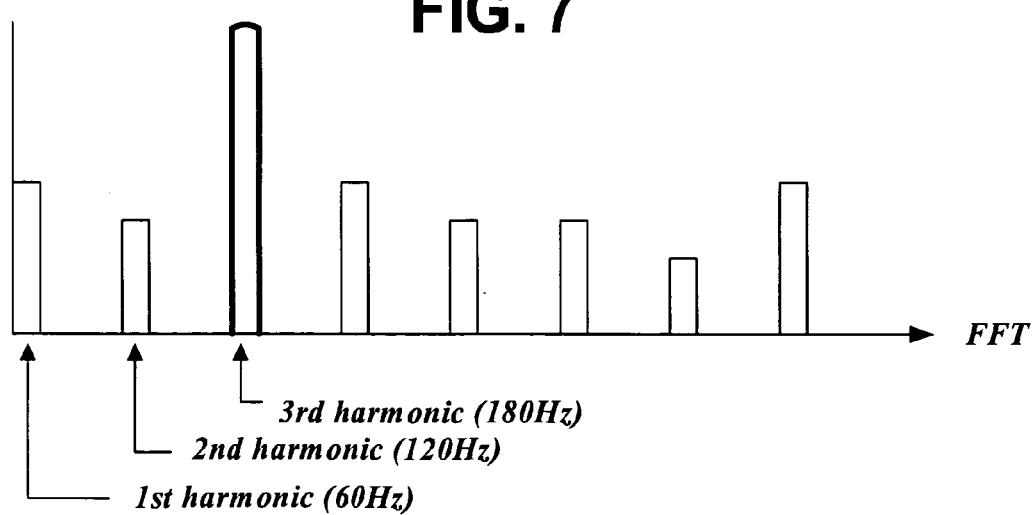
FIG. 7 illustrates a frequency spectrum of stray current caused by an imbalanced load condition.
Figure 8:
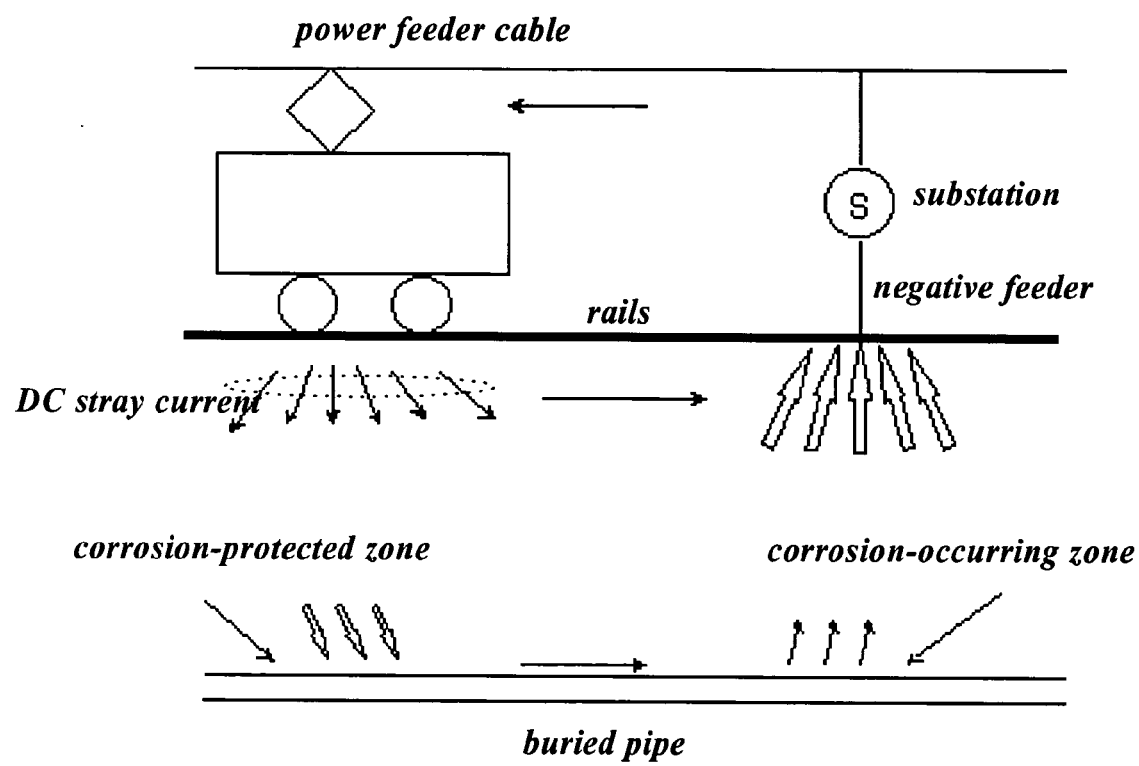
FIG. 8 illustrates an interference mechanism by stray currents from subway rails.
Figure 9:
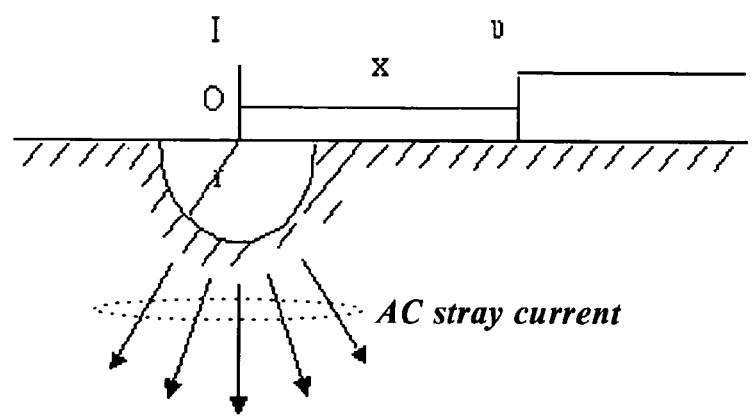
FIG. 9 illustrates a resistive induction mechanism by stray currents from power lines.
Figure 10:
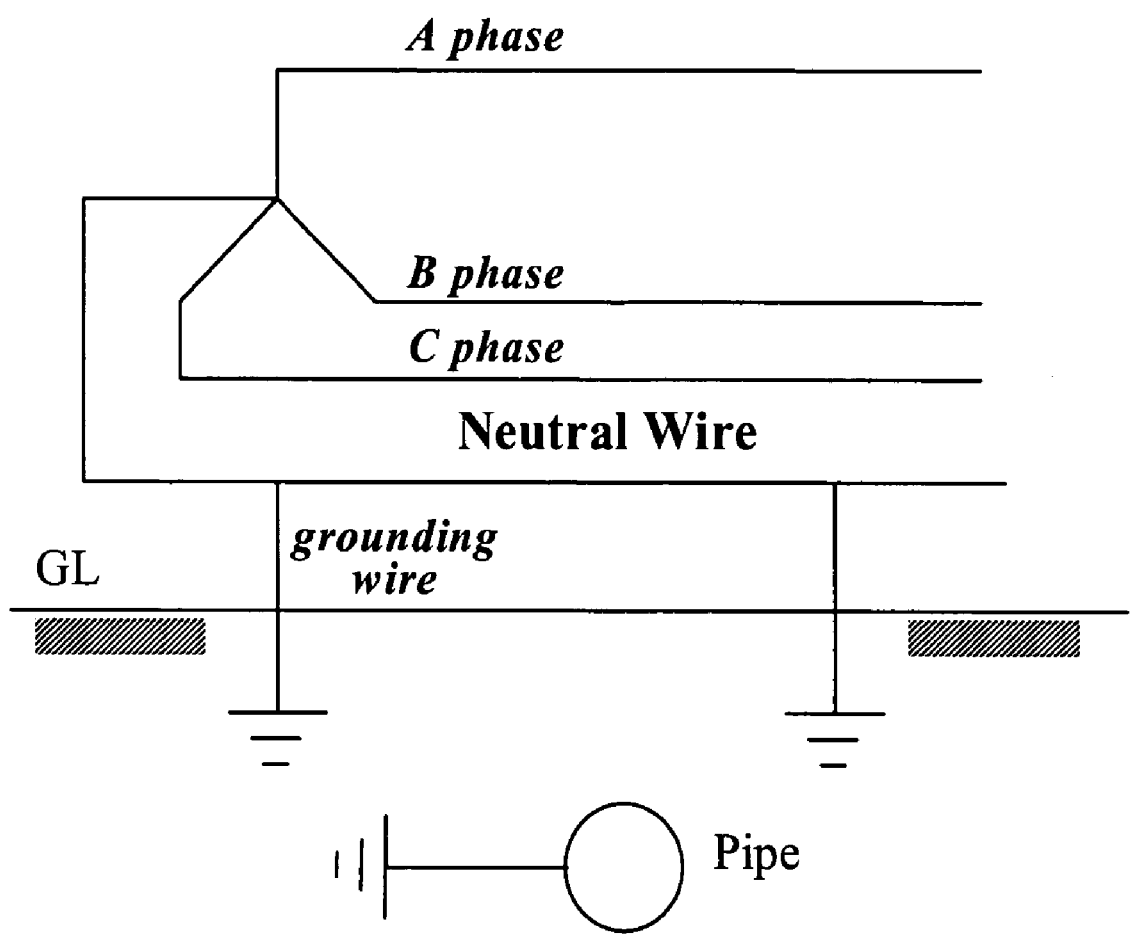
FIG. 10 illustrates a 3-phase and 4-wire distribution system.

The measurement of the stray currents is, as illustrated in FIG. 5, conducted at an impedance bond of the subway rails 20 and converter negative feeder for subway or at the grounding wire of a neutral wire of a power distribution line for power lines. The stray currents data stored in the memory 120 is transmitted to the analyzing computer terminal 300 through the communication port 122 and the charging and communication module 200 according to a predefined communication protocol. In the analyzing computer terminal 300, the received data is databased and stored in the hard disk drive 308.

The pipe-to-soil voltage measured from the test box 30 at a specific position of the buried metallic structure is digitized by the A/D converter 108 and stored in the memory 120. The digitized data is transmitted through the communication port 122 to the analyzing computer terminal 300 in which the data is databased and stored in the hard disk drive 308.

The measured stray currents data is synchronized with pipe-to-soil voltage data by the application program 310 and thus the two waveforms can be displayed and analyzed simultaneously. It is determined that the waveforms of the soil-to-voltage data and stray currents are in phase or out of phase.

If the stray currents from the subway rails or power lines leak into a buried metallic structure, the two waveforms show the same trend but are out of phase. Therefore, the analysis results are utilized to determine whether the buried metallic structure is protected from corrosion.

It is desired that the measuring module 100 be waterproof so that it can be installed outdoors.

The apparatus with storage for measuring stray currents from subway rails or power lines and the pipe-to-soil voltage of a buried metallic structure in accordance with the present invention allows simultaneous measurement of stray currents from subway rails or power lines and pipe-to-soil voltage of the buried metallic structure and makes it easy to analyze relationship between the stray currents and pipe-to-soil voltage.

While the invention has been disclosed with respect to a limited number of embodiments, those skilled in the art, having the benefit of this disclosure, will appreciate numerous modifications and variations therefrom. It is intended that all such modifications and variations fall within the spirit and scope of the invention.

What is claimed is:

1. A data measuring apparatus with storage for measuring stray currents from subway rails or power lines and the pipe-to-soil voltage of a buried metallic structure, comprising:

measuring means, which is a portable module that allows easy installation at one or multiple measurement points of the buried metallic structure, for measuring stray currents from the subway rails or power lines and the pipe-to-soil voltage of the buried metallic structure simultaneously and for storing and transmitting the measurement data, said measuring means comprising a clamp-on type current sensor (114) that can be attached to a power feeder cable connected to said subway rails; and analytic computing means for receiving the measurement data transmitted from the measuring means and for databasing and graphically displaying the received measurement data for time-synchronous data analysis.

2. The data measuring apparatus set forth in claim 1, wherein the measuring means comprises:

a function input unit for receiving a function input for performing the measurement of the stray currents and pipe-to-soil voltage;

an A/D converter for digitizing stray currents detected by current sensors installed at the subway rails and power lines and for digitizing the pipe-to-soil voltage measured from a test box installed at the buried metallic structure;

a main processor unit for controlling the process of storing the digitized stray current data and pipe-to-soil voltage data and transmitting the digital data to the analytic computing means;

a memory for storing the digitized stray current data and pipe-to-soil voltage data; and a communication port, controlled by the main processor unit, for performing communication with the analytic computing means to transmit the digitized stray current data and pipe-to-soil voltage data.

3. The data measuring apparatus set forth in claim 2, wherein the measuring means further comprises a DC/DC converter for providing power required for the operation of the measuring means and the current sensors by DC/DC converting an input DC power from an external source.

4. The data measuring apparatus set forth in claim 2, wherein each of the current sensors is equipped with a battery pack for a long-time measurement operation.

5. The data measuring apparatus set forth in claim 2, wherein the communication port is either a wired communication port or a wireless communication port.

6. The data measuring apparatus set forth in claim 1, further comprising a charging and communication module, which is connected between the measuring means and the analytic computing means and powered by the analytic computing means, for powering the measuring means and for acting as a communication interface between the measuring means and the analytic computing means.

7. The data measuring apparatus set forth in claim 6, wherein the charging and communication module comprises a wireless or wired communication port, which is connected between the measuring means and the analytic computing means, for performing wireless or wired communication with the measuring means and the analytic computing means.

8. The data measuring apparatus set forth in claim 1, wherein the analytic computing means is equipped with an application program for databasing and storing the measurement data of stray currents and pipe-to-soil voltage provided from the measuring means so that the measurement data may be searched based on the measurement date and the station at which the measuring means is installed and for graphically displaying the databased measurement data so that time-synchronous analysis of the waveforms of the stray currents and pipe-to-soil voltage may be conducted.

9. The data measuring apparatus set forth in claim 1, wherein if multiple measuring means are installed at multiple subway stations, the analytic computing means can identify the multiple measuring means based on the ID of each measuring means and the databased measurement data is stored in such a way that a search for the measurement data of each measuring means can be performed based on the ID of the measuring means.

10. The data measuring apparatus set forth in claim 1, wherein the analytic computing means further comprises an output port for data communication with an external apparatus and allows the measurement data to be printed by an external printer, to be displayed by LED or LCD, to be stored in an external storage device, or to be displayed by an external displaying apparatus through the output port.

11. The data measuring apparatus set forth in claim 1, wherein the measuring means detects current changes in the power feeder cable using the current sensor attached to selected positions of the power feeder cable and conducting measurement at an impedance bond of the rails and a converter negative feeder.

12. The data measuring apparatus set forth in claim 1, wherein the measuring means further measure stray currents using voltage across a shunt resistor connect to the power feeder cable from a converter.

* * * * *